(12) United States Patent
Freeman et al.

(10) Patent No.: US 6,701,032 B1
(45) Date of Patent: Mar. 2, 2004

(54) DEVICE FOR HOUSING A PLANAR OPTICAL COMPONENT

(75) Inventors: Neville John Freeman, Tarporley (GB); Benharrat Bouattou, Manchester (GB)

(73) Assignee: Farfield Sensors Limited (GB)

( * ) Notice: Subject to any disclaimer, the term of this patent is extended or adjusted under 35 U.S.C. 154(b) by 0 days.

(21) Appl. No.: 09/701,821
(22) PCT Filed: May 27, 1999
(86) PCT No.: PCT/GB99/01465
§ 371 (c)(1),
(2), (4) Date: Apr. 2, 2001
(87) PCT Pub. No.: WO99/63330
PCT Pub. Date: Dec. 9, 1999

(51) Int. Cl.$^7$ .................................................. G02B 6/00
(52) U.S. Cl. ........................................................ 385/12
(58) Field of Search ............................. 385/10–12, 18, 385/19, 88, 90–94

(56) References Cited

U.S. PATENT DOCUMENTS

| | | | |
|---|---|---|---|
| 4,703,182 A | 10/1987 | Kroneis et al. .......... 250/458.1 |
| 4,767,174 A | 8/1988 | Carenco et al. ............ 350/96.2 |
| 4,810,658 A | 3/1989 | Shanks et al. ............... 436/172 |
| 5,036,220 A | * 7/1991 | Byer et al. .................... 307/427 |
| 5,049,762 A | * 9/1991 | Katoh ......................... 359/332 |
| 5,082,629 A | 1/1992 | Burgess, Jr. et al. ..... 422/82.11 |
| 5,107,537 A | * 4/1992 | Schriks et al. ................. 385/91 |
| 5,175,784 A | * 12/1992 | Enomoto et al. ........... 385/122 |
| 5,347,604 A | * 9/1994 | Go et al. ....................... 385/92 |
| 5,369,717 A | 11/1994 | Attridge ...................... 385/12 |
| 5,692,085 A | 11/1997 | Jongerius et al. ............. 385/91 |

FOREIGN PATENT DOCUMENTS

| | | |
|---|---|---|
| WO | WO 94/27137 | 11/1994 |
| WO | WO 98/22807 | 5/1998 |

* cited by examiner

Primary Examiner—Jean F. Duverne
(74) Attorney, Agent, or Firm—Factor & Partners

(57) ABSTRACT

A device for housing a planar optical component such as a chemical sensor comprising a holder for mounting a planar optical component, a housing adapted to receive internally said holder along a longitudinal axis, and guiding means for correlating the position of said planar optical component and of a source of electromagnetic radiation when said holder is located within said housing.

29 Claims, 8 Drawing Sheets

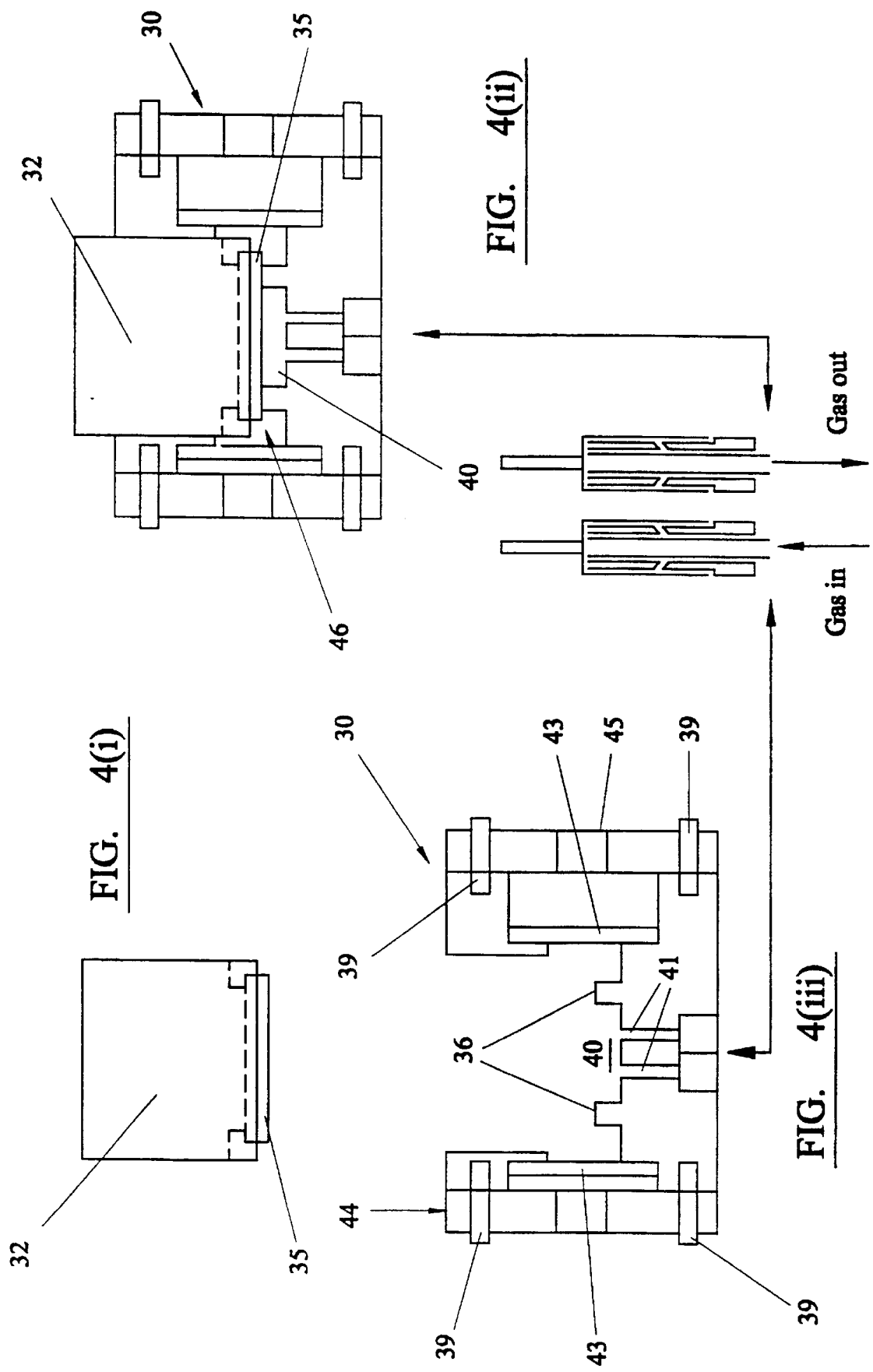

DEVICE FOR HOUSING A PLANAR OPTICAL COMPONENT

The present invention relates to an improved device for housing a planar optical component such as a chemical sensor for example.

New chemical sensor technologies using optical techniques (in particular interferometric techniques) are providing new high performance devices. Whilst these devices are relatively simple in terms of components, the tolerances required in the assembly procedure can be extremely onerous. Of these, end illuminated interferometric devices are perhaps the most demanding. In such cases, sub-micron misalignment between the electromagnetic radiation source (typically a collimated, focussed laser) and the sensor substrate itself may be sufficient to prevent its correct operation.

There are several situations which may lead to distorted output from a prior art device. Thus, the light beam may pass over the top of the planar optical component and distort the output received by the detector. Similarly, where the device comprises a planar sensing waveguide and a planar reference waveguide, if the light misses a waveguide or fails to illuminate both equally, the output may be lost or distorted. Thus, If any of the components (eg light source, lenses, polarisers, sensors etc) are misaligned by as little as $2 \times 10^{-7}$ meters (200 nm) the performance of the device will be adversely effected. The provision of a device which ensures that waveguides are illuminated equally without admitting stray light represents a significant technical challenge.

More generally, there is a need for sensor assemblies of simpler construction and improved reliability. The range and applicability of chemical sensors could be greatly enhanced if it were possible to achieve lower manufacturing costs and greater robustness.

The present invention seeks to provide an improved device for housing a chemical sensor. The device is advantageously robust and gives enhanced signal to noise ratios (sensitivity) and has the ability to provide self diagnosis (thus predicting its own suitability to function as a chemical sensor) Moreover, the invention seeks to provide an optical (interferometric) chemical sensor device which is simple to assemble and fault tolerant in terms of construction errors and which may be used to obtain reliable information relating to the changes occurring within the device.

Thus viewed from one aspect the present invention provides a device comprising:

- a holder for mounting a planar optical component (eg a chemical sensor);
- a housing adapted to receive internally said holder so as to define a longitudinal path through the device in which the planar optical component is effectively exposed in free space; and
- guiding means for correlating along said longitudinal path the position of said planar optical component and of a source of electromagnetic radiation when said holder is located within said housing, whereby to expose said planar optical component to said electromagnetic radiation along said longitudinal path whilst substantially eliminating stray electromagnetic radiation.

The exclusion of stray radiation enables the number of components to be minimised and enables straightforward analysis of the signals generated by the planar optical component (such as the centre of gravity of a series of interferometric fringes for example). This is achieved by ensuring that electromagnetic radiation excites substantially only the planar optical component. The device of the invention is suitable for the fault tolerant construction of planar optical sensors and ensures optimal performance from the planar optical component. Tolerances are typically reduced by approximately 1000 fold enabling cheap mass production methods such as compression moulding and injection moulding to be employed.

In a preferred embodiment, the device according to the invention comprises a planar optical component having a plurality of waveguides. Typically the planar optical component comprises a sensing waveguide and a reference waveguide. Preferably the planar optical component is any of those described in WO-A-98/22807 (IMCO (1097) Ltd et al)

Preferably the housing is provided with one or more seats upon which the planar optical component may be seated when the housing and holder are assembled.

Preferably the holder comprises a basal recess in which the planar optical component may be mounted. To ensure that the edge of the planar optical component which is to be excited by the electromagnetic radiation is suitably exposed in the longitudinal path, one or more longitudinal cavities may be provided in the base of the holder such that when the planar optical component is positioned adjacent an aperture in the housing, the majority of the leading and trailing edges of the planar optical component may be exposed in free space.

Preferably the device of the invention comprises a guiding means in the form of a spacer incorporated in the planar optical component or in the housing itself. In the first instance, the spacer may be incorporated in the planar optical component conventionally during manufacture. In the second instance, the spacer takes the form of (or is located on) a seat in the housing upon which the planar optical component is located in use. This latter embodiment has the advantages that the sensing layer of the planar optical component is more efficiently exposed to the test material, that the manufacture of the planar optical component is simplified and that the disturbance of the planar optical component (as a result of bringing it into contact with the seat or with the modified seat upon which the spacer is located) is minimised. The material from which the spacer is made is judiciously chosen in terms of refractive index and physical properties. The spacer is advantageously permeable to the sample under analysis.

In a first particularly preferred embodiment, the housing comprises a first aperture at a first end of a longitudinal path for admitting electromagnetic radiation and a second aperture at a second end of said longitudinal path for transmitting electromagnetic radiation. Provided the spacer is of a known predetermined thickness relative to the known distance between the first aperture and the surface upon which the planar optical component is seated within the housing, electromagnetic radiation may be effectively guided onto the waveguides.

In a second particularly preferred embodiment, the planar optical component and incorporated spacer may be located on a silicon baseplate. The silicon baseplate which is typically optically flat may be conveniently provided with a hole over which the planar optical component is located. Conveniently, the spacer may seal the hole in the baseplate provided the spacer is sufficiently (eg optically) flat.

In an especially preferred embodiment, the silicon baseplate is provided with a channel (eg a V-shaped channel) capable of receiving an optical fibre wherein the depth of the channel predetermines the position and height that electromagnetic radiation is emitted relative to the surface of the silicon baseplate. Since the position of the waveguides above the surface of the silicon baseplate is determined by the height of the incorporated spacer, the position of the electromagnetic radiation and the waveguides may be correlated. Stray light is simply emitted into the silicon.

In an alternative especially preferred embodiment, the silicon baseplate forms part of an integrated electro-optic device in which a laser source is integrated into the silicon baseplate. The guiding means is provided by an incorporated spacer located on the silicon baseplate or the planar optical component as hereinbefore described.

In either of the especially preferred embodiments, the output may be monitored by a discrete detector or an imaging fibre or fibre array may be used to collect the output image. Alternatively, a photodetector could be integrated into the silicon structure. Using fibres in and out is very useful in safety critical applications (ie there is no electricity).

In a preferred embodiment of the invention, the holder is removably received in the housing. The provision of a holder of this type advantageously enables the planar optical component (eg sensor) to be replaced without discarding or rebuilding the supporting components.

Preferably, the housing in the device of the invention comprises means (eg a flat surface, one or more seats or seals) for providing a gas or liquid seal to the surface of the planar optical component to allow transport of the analyte to and from the planar optical component and measurement of the optical behaviour of the component in the presence of the analyte. The provision of a seal to the surface of the sensor reduces the dead volume to a minimum (this is important in providing optimal performance with chemical sensors). The provision of a seal to the surface of the sensor also enables liquid samples to be used in addition to gas samples. This is not conceivable with a conventional freestanding arrangement as wetting of the end faces would lead to optical misalignment.

Preferably, the housing is capable of mounting an electromagnetic radiation source. Preferably, the housing is capable of mounting an electromagnetic radiation detection device. Preferably, the device of the invention comprises means for the provision of removable or non-removable components between the planar optical component (eg chemical sensor) and a source of electromagnetic radiation and/or between the planar optical component and a radiation detection device. Such components may be conventional lenses, polarisers, electromagnetic radiation windows, etc mounted in a conventional manner. Optionally, the device of the invention provides a means for providing a constant force between the holder and the housing.

In all cases, the body of the housing and holder are preferably opaque to minimise stray electromagnetic radiation. Thus the planar optical component may be advantageously mounted on a platform which does not transmit electromagnetic radiation, thereby preventing stray electromagnetic radiation passing thereunder. Preferably, the seat or seal of the housing also may not transmit electromagnetic radiation in the longitudinal direction whereby to further prevent stray electromagnetic radiation passing over the sensor surface and reaching the detector. Preferably, the seat or seal has an inlet, a channel and an outlet providing a means through which analyte (eg gases or liquids) may pass. In this way, analyte is able to pass into and out of the absorbent layers of a planar optical component (eg chemical sensor) leading to measurable changes in the output electromagnetic radiation. Preferably, the extremes (edges) of the sensor are sealed from the environment to prevent extraneous effects from gases, vapours or liquids from external sources not related to the sample under analysis.

Viewed from a further aspect the present invention provides the use of a device as hereinbefore described as a gas or liquid sensor.

The invention will now be described in preferred embodiments in a non-limitative sense with reference to the accompanying FIGS. in which:

FIG. 4 illustrates an exploded view of a cross-section of a disassembled embodiment of the device according to the invention;

Figure 1:
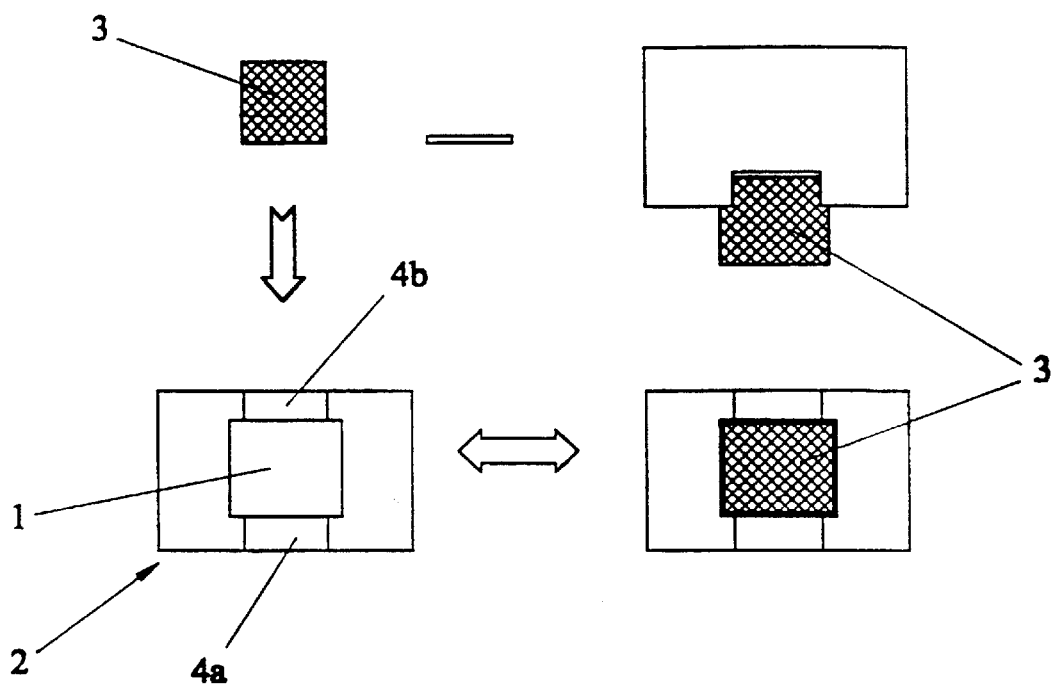
FIG. 1 illustrates a bottom view of the holder in accordance with the invention.

FIG. 1 illustrates a holder 2 in which the planar optical component (sensor or sample) 3 is mounted in a basal recess 1. Longitudinal cavities 4a and 4b are provided along a longitudinal path to allow the sensor to be positioned adjacent the aperture in the housing so as to ensure that the majority of the leading and trailing edges of the sensor are exposed in free space.

Figure 2:
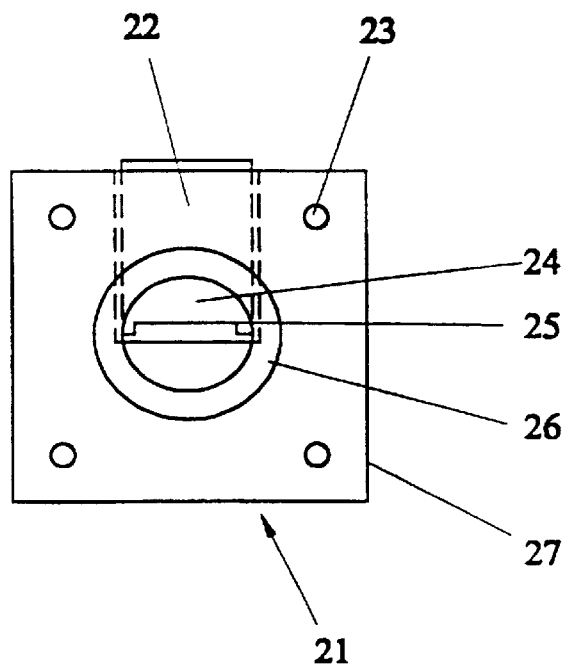
FIG. 2 illustrates an end elevation of the holder positioned within the housing in accordance with the invention.

FIG. 2 shows an end elevation of the device 21 with the holder 22 positioned within the housing 27 in such a manner as to expose a longitudinal path into the housing, through to the planar optical component and out of the housing (not shown). The end face of the housing has dowel holes (one of four is designated with numeral 23) to enable the reliable and accurate location of additional plates upon which may be mounted electromagnetic radiation sources (such as a laser diode for example), electromagnetic radiation detectors (such as a photodiode arrays for example) and other optional components such as lenses. The housing has a circular aperture 24 which allows the electromagnetic radiation to pass therethrough (to the planar waveguide chemical sensor 25). The aperture also has a recess 26 which enables a window capable of transmitting the electromagnetic radiation to be fitted. This ensures that the sensor is sealed from the surroundings in terms of potential chemical interference. A means for transporting the analyte to the sensor structure has been omitted from this Figure for the sake of clarity.

Figure 3:
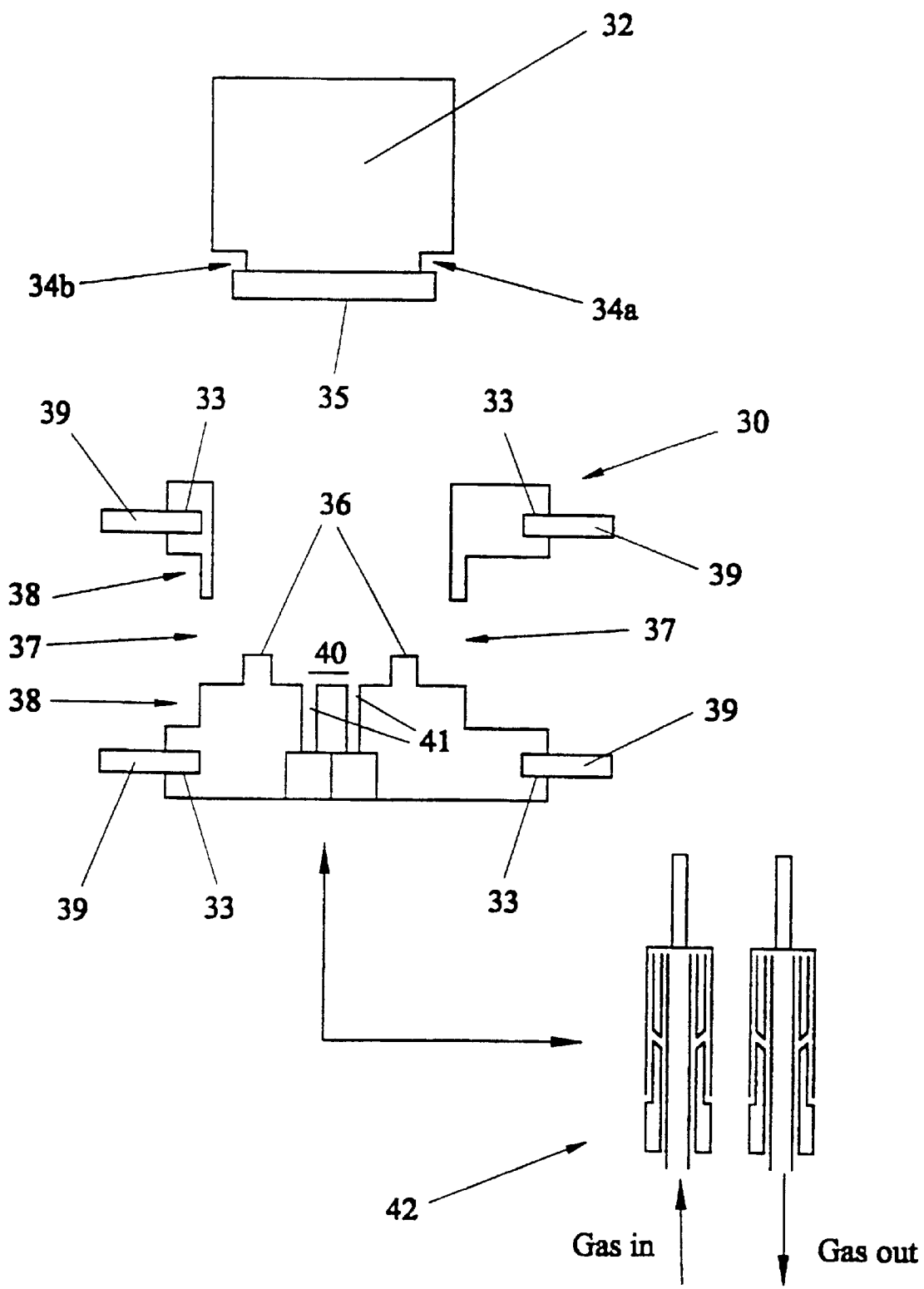
FIG. 3 illustrates in cross-section a disassembled embodiment of the device according to the invention.

An exploded cross-section of an embodiment of the device is provided in FIG. 3. Shown removed from the housing 30 are the sensor holder 32 and sensor 35 with longitudinal cavities 34a and 34b allowing the majority of the leading and trailing edges of the sensor to be exposed in free space. The sensor 35 is inserted into the housing 30 such that the top surface of the sensor 35 makes contact and seals (in a gas/liquid type manner) with the sensor housing seat 36. The apertures 37 for the passage of electromagnetic radiation and the recesses for the windows 38 allow the transmission of electromagnetic radiation. The windows themselves have been omitted for the sake of clarity. The dowel holes 33 are shown occupied by dowels 39. The channel 40 for the passage of analyte over the surface and the conduits 41 for the transmission of the analyte to and from the sensor surface are shown. In this embodiment, the conduits 41 are terminated with ¼" 28 UNF inverted cone fittings. (made by OMNIFIT) 42 to provide a mechanical connection to the desired test source.

FIG. 4 shows in detailed cross-section an embodiment of the invention. FIG. 4ii shows the housing 30 with the holder 32 and sensor 35 removed. The holder 32 and sensor 35 are shown separately in FIG. 4i. The housing is shown in FIG. 4iii with windows 43 and a plate mounted with a laser diode 44 and a plate mounted with a photodetector array 45. The precise location of the plates is achieved by the dowels 39. The housing seat 36, the channel for test materials 40 and the conduits 41 are as hereinbefore described. FIG. 4ii shows the complete assembly with the holder in place in the housing. The positioning of holder 32 in housing 30 creates a dead volume 40. The volume around the ends of the sensor 46 is minimised to reduce effects due to external or ambient chemical changes. FIG. 4iii shows the inverted cone fittings for connection to the device of the invention and transmission of analyte.

Figure 5I:
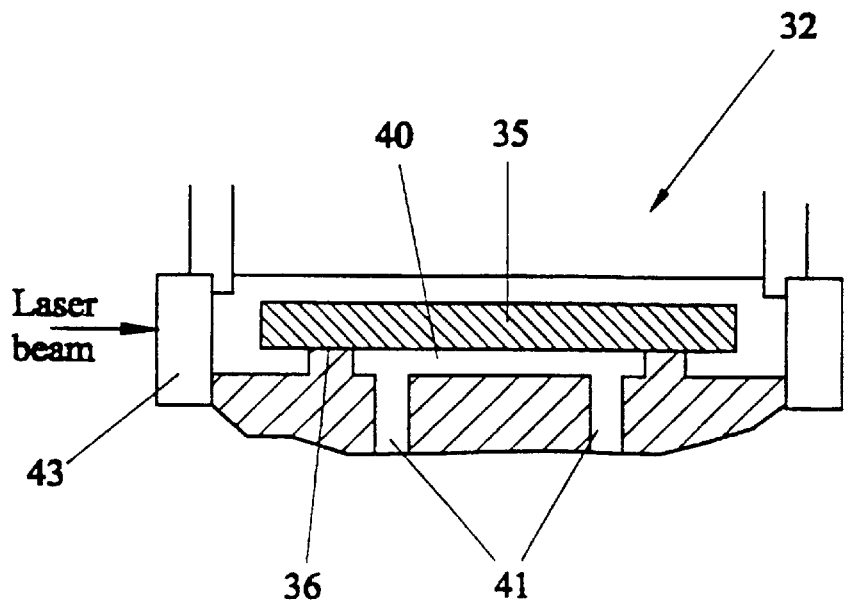
FIG. 5 illustrates a top view of the housing and a partial side view of the holder within the housing in accordance with one embodiment of the invention.
Figure 5:
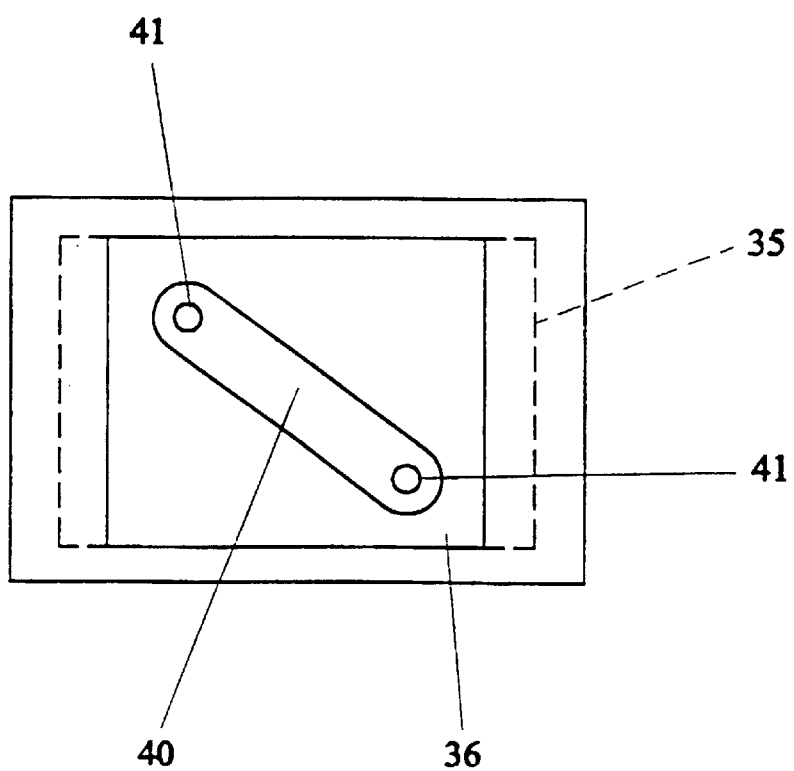

FIGS. 5i and 5ii show a partial cross-section and plan view respectively of the sensor housing seat which seals to the surface of the sensor. The seat or seal 36 provides a complete gas tight seal to the surface of the sensor 35. The conduits 41 allow the passage of test analyte to and from the sensor surface via the channel 40 which allows the analyte to come into intimate contact with the sensor surface.

Figure 6:
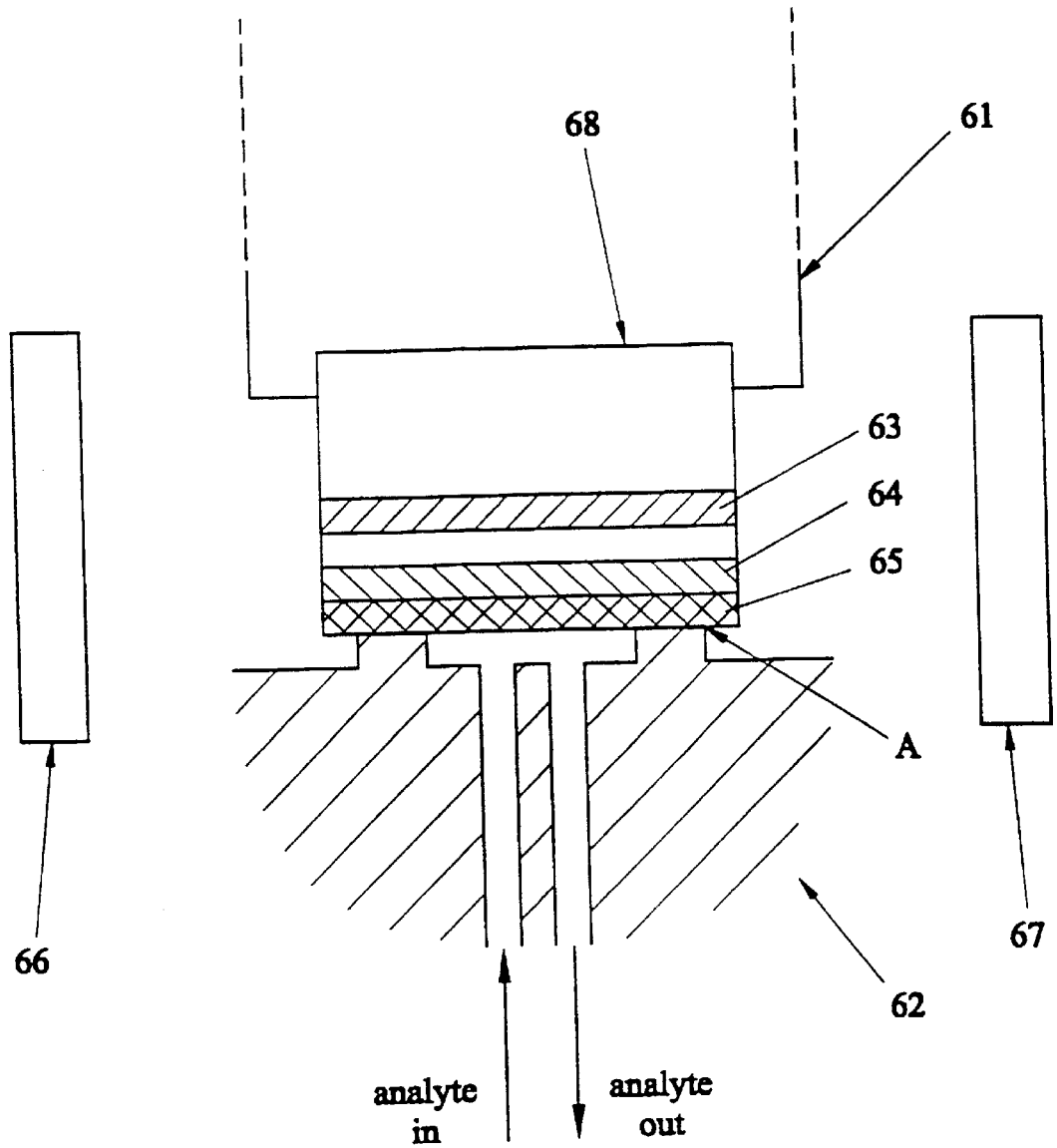
FIG. 6 illustrates an embodiment of the invention.

FIG. 6 illustrates an assembled holder 61 and housing 62. The sensor 68 comprises waveguides 63 and 64 together with a spacer 65 which may be deposited when the sensor is manufactured. Provided the spacer thickness and height of surface A are known relative to the position of electromagnetic radiation source 66, the electromagnetic radiation will fall substantially wholly on the waveguides. The holder and housing are made opaque to the wavelength of electromagnetic radiation to reduce stray output to the detector 67. Engineering tolerances are around 200 μm.

Figure 9:
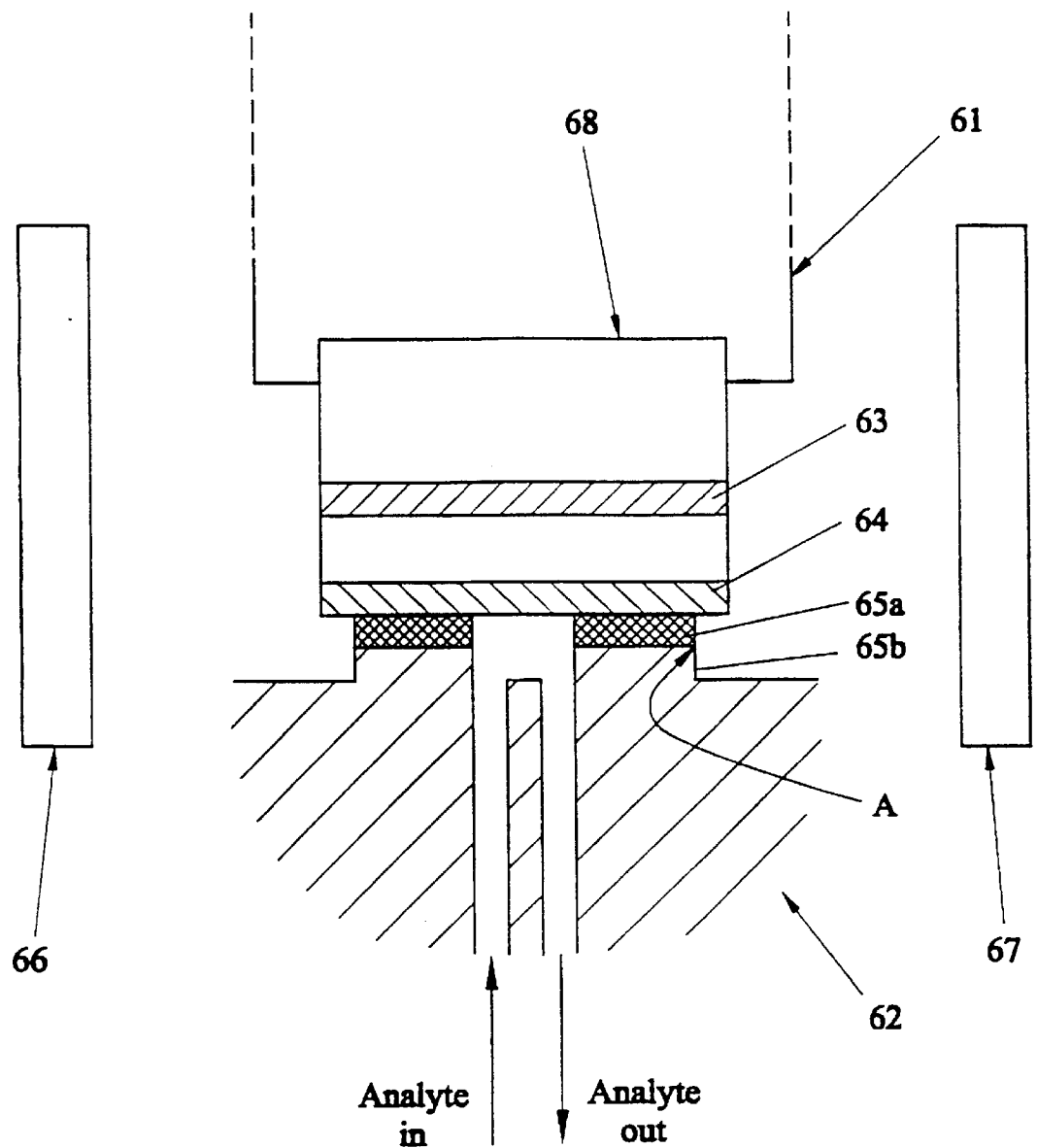
FIG. 9 illustrates a further embodiment of the invention.

FIG. 9 illustrates an assembled holder 61 and housing 62 similar to FIG. 6 but with the spacer 65a provided on the seats 65b. This improves the exposure of the sensing layer to test material.

Figure 7:
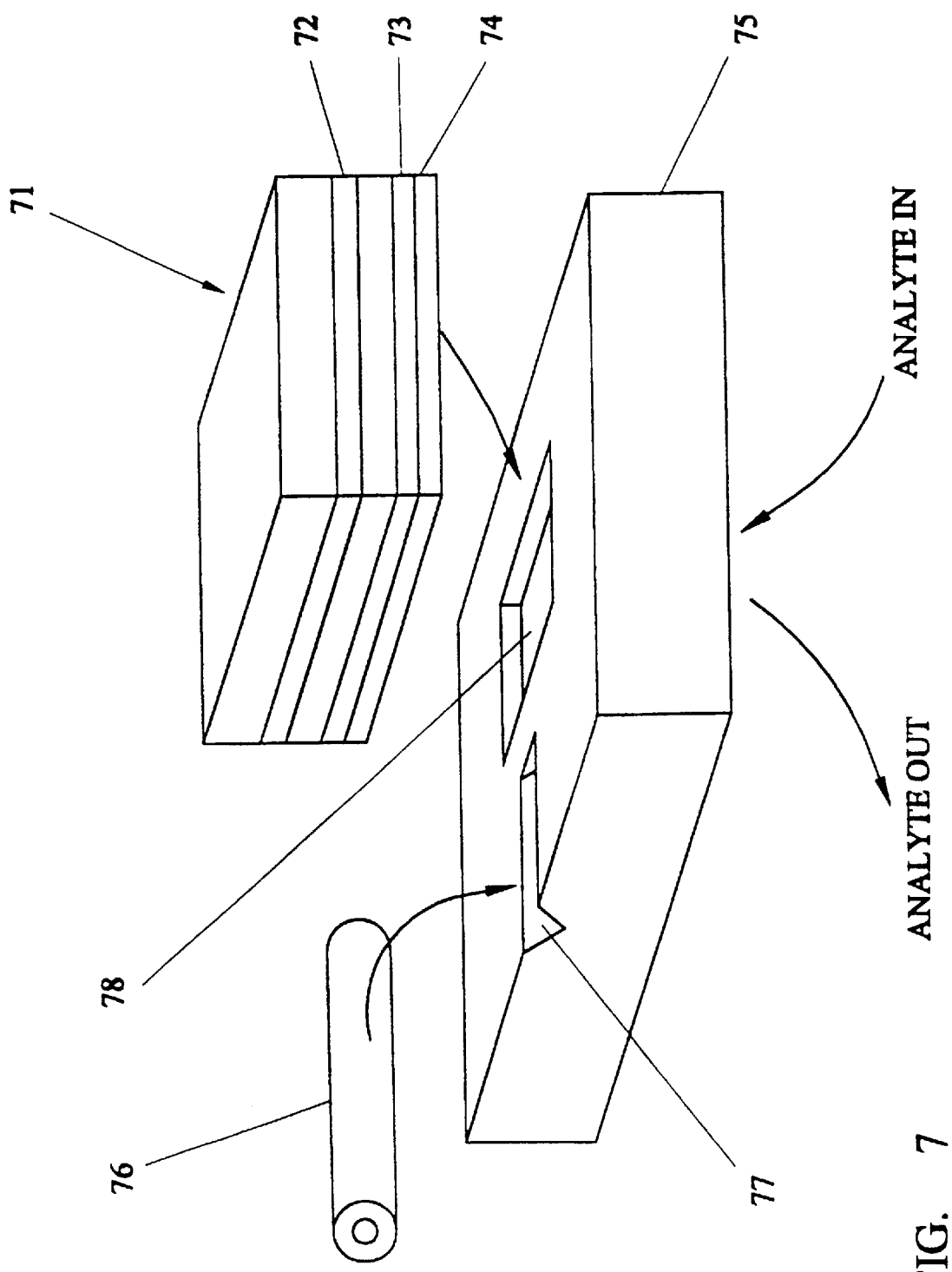
FIG. 7 illustrates a further embodiment of the invention.

In the embodiment of FIG. 7, the sensor 71 is provided with reference and sensing waveguides (72 and 73), spacer 74 and a silicon baseplate 75. Optical fibre 76 is located in a V-groove 77 of baseplate 75. The position and height of the emitted light relative to the silicon baseplate is determined by the V-groove. The baseplate has hole 78 etched in it over which the sensor is located. The height of the waveguide relative to light from the fibre is set by the spacer which additionally seals the hole 78 by being sufficiently flat. Stray light is emitted into the silicon. A discrete detector may be used to monitor output or an imaging fibre or fibre array may be used to collect output images, or a detector system may be incorporated (integrated) in the baseplate.

Figure 8:
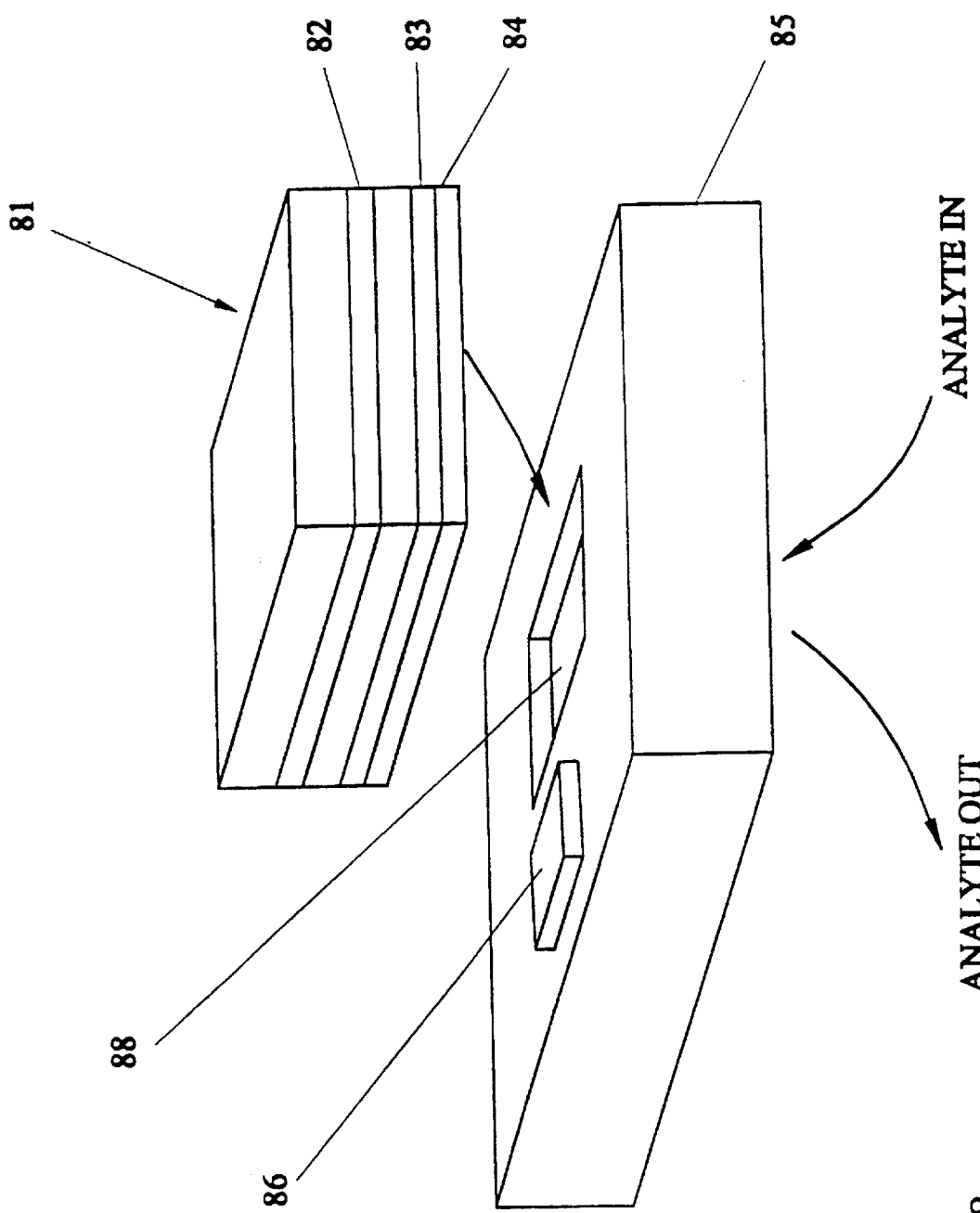
FIG. 8 illustrates a further embodiment of the invention.

In the embodiment of FIG. 8, the sensor 81 is provided with reference and sensing waveguides 82 and 83, a spacer 84 and a silicon baseplate 85. Laser 86 is integrally located in the silicon baseplate. Thus, this embodiment represents an integrated electro-optic device in which the laser source 86 is integrated in the silicon baseplate. Output may be discrete, integrated or fibre optic as described hereinbefore.

What is claimed is:

1. A device for exposing a planar optical component to electromagnetic radiation comprising:
    a holder for mounting the planar optical component;
    a housing adapted to receive internally said holder so as to define a longitudinal path through the device in which the planar optical component is effectively exposed in free space; and
    guiding means comprising a spacer incorporated in one of the planar optical component and the housing, the guiding means being capable of correlating along said longitudinal path the position of said planar optical component and of a source of electromagnetic radiation when said holder is located within said housing, whereby to expose said planar optical component to said electromagnetic radiation along said longitudinal path whilst substantially eliminating stray electromagnetic radiation.

2. A device as claimed in claim 1 wherein said planar optical component is a chemical sensor.

3. A device as claimed in claim 1, wherein said planar optical component comprises a plurality of waveguides.

4. A device as claimed in claim 3, wherein said planar optical component comprises a sensing waveguide and a reference waveguide.

5. A device as claimed in claim 1, wherein said housing comprises a first aperture at a first end of a transverse axis for admitting electromagnetic radiation and a second aperture at a second end of said transverse axis for transmitting electromagnetic radiation.

6. A device as claimed in claim 1, wherein said planar optical component and incorporated spacer are located on a silicon baseplate.

7. A device as claimed in claim 6, wherein said planar optical component is located over an aperture in the silicon baseplate.

8. A device as claimed in claim 6, wherein said silicon baseplate is provided with a channel capable of receiving an optical fibre.

9. A device as claimed in claim 6, wherein said silicon baseplate forms part of an integrated electro-optic device in which a laser source is integrated into the silicon baseplate.

10. A device as claimed in claim 1, wherein said holder is detachably received in the housing.

11. A device as claimed in claim 1, wherein said housing comprises sealing means for providing a gas or liquid seal to the surface of the planar optical component.

12. A device as claimed in claim 11 wherein said sealing means comprises one or more conduits capable of permitting transport of analyte to and from the planar optical component whereby to enable measurement of the optical behaviour of the planar optical component in the presence of the analyte.

13. A device as claimed in claim 1, wherein said holder comprises a basal recess at or near to its base in which the planar optical component may be mounted.

14. A device as claimed in claim 1, wherein the base of said holder further comprises one or more longitudinal cavities such that when the planar optical component is positioned adjacent an aperture in the housing the majority of the leading and trailing edges of the planar optical component may be exposed in free space.

15. A device as claimed in claim 1 wherein said spacer takes the form of or is located upon a seat in the housing upon which the planar optical component is located in use.

16. A device for exposing a planar optical component to electromagnetic radiation, comprising:
    a holder comprising a base and a basal recess at or near to the base for mounting a planar optical component;
    a housing adapted to receive internally said holder so as to define a longitudinal path through the device in which the planar optical component is effectively exposed in free space; and
    guiding means for correlating along said longitudinal path the position of said planar optical component and of a source of electromagnetic radiation when said holder is located within said housing, whereby to expose said planar optical component to said electromagnetic radiation along said longitudinal path whilst substantially eliminating stray radiation, wherein said guiding means is one or more longitudinal cavities in the base of said holder such that when the planar optical component is positioned adjacent an aperture in the housing the majority of the leading and trailing edges of the planar optical component are exposed in free space.

17. A device as claimed in claim 16 wherein said planar optical component is a chemical sensor.

18. A device as claimed in claim 16 wherein said planar optical component comprises a plurality of waveguides.

19. A device as claimed in claim 18, wherein said planar optical component comprises a sensing waveguide and a reference waveguide.

20. A device as claimed in claim 16, wherein said guiding means is a spacer incorporated in the planar optical component or in the housing.

21. A device as claimed in claim 16, wherein said housing comprises a first aperture at a first end of a transverse axis for admitting electromagnetic radiation and a second aperture at a second end of said transverse axis for transmitting electromagnetic radiation.

22. A device as claimed in claim 20, wherein said planar optical component and incorporated spacer are located on a silicon baseplate.

23. A device as claimed in claim 22, wherein said planar optical component is located over an aperture in the silicon baseplate.

24. A device as claimed in claim 22, wherein said silicon baseplate is provided with a channel capable of receiving an optical fibre.

25. A device as claimed in claim 22, wherein said silicon baseplate forms part of an integrated electro-optic device in which a laser source is integrated into the silicon baseplate.

26. A device as claimed in claim 16, wherein said holder is detachably received in the housing.

27. A device as claimed in claim 16, wherein said housing comprises sealing means for providing a gas or liquid seal to the surface of the planar optical component.

28. A device as claimed in claim 27 wherein said sealing means comprises one or more conduits capable of permitting transport of analyte to and from the planar optical component whereby to enable measurement of the optical behaviour of the planar optical component in the presence of the analyte.

29. A device as claimed in claim 20 wherein said spacer takes the form of or is located upon a seat in the housing upon which the planar optical component is located in use.

* * * * *